United States Patent [19]

Hannart

[11] Patent Number: 4,617,305
[45] Date of Patent: Oct. 14, 1986

[54] 4-ALKYLINDOLONAPHTHYRIDINES AND THEIR THERAPEUTICAL APPLICATION

[75] Inventor: Jean A. A. J. Hannart, Dion-Valmont, Belgium

[73] Assignee: Omnichem, S.A., Belgium

[21] Appl. No.: 582,314

[22] Filed: Feb. 22, 1984

[30] Foreign Application Priority Data

Feb. 25, 1983 [LU] Luxembourg ............................ 84664

[51] Int. Cl.$^4$ .................. C07D 471/16; A61K 31/475
[52] U.S. Cl. ..................................... 514/278; 514/288; 546/18; 546/66
[58] Field of Search ..................... 546/66, 18; 424/256; 514/278, 288

[56] References Cited

U.S. PATENT DOCUMENTS

| | | | |
|---|---|---|---|
| 4,190,657 | 2/1980 | Koletar et al. | 546/66 |
| 4,200,638 | 4/1980 | Hannart | 546/66 |
| 4,218,453 | 8/1980 | Hannart | 546/66 |

FOREIGN PATENT DOCUMENTS

| | | | |
|---|---|---|---|
| 761628 | 1/1971 | Belgium . | |
| 799679 | 9/1973 | Belgium . | |
| 816759 | 10/1974 | Belgium . | |
| 848475 | 3/1977 | Belgium . | |
| 882024 | 9/1980 | Belgium . | |
| 884145 | 1/1981 | Belgium . | |
| 43811 | 1/1981 | European Pat. Off. | 546/66 |
| 0064317 | 10/1982 | European Pat. Off. . | |
| 2758404 | 7/1978 | Fed. Rep. of Germany | 514/288 |
| 2449449 | 10/1980 | France | 514/288 |
| 2068731 | 8/1981 | United Kingdom | 514/288 |
| 2120250 | 11/1983 | United Kingdom | 546/66 |

OTHER PUBLICATIONS

Lajos Novak, Janos Rohaly and Csaba Szantay, "Synthesis of Vinca Alkaloids and Related Compounds VI$^1$", Heterocycles, vol. 6, No. 8, 1977, pp. 1149–1157.
J. T. Litchfield, Jr. and F. Wilcoxon, "A Simplified Method of Evaluating Dose–Effect Experiments", The Journal of Pharmacology and Experimental Therapeutics, pp. 99–113.
Le Men et al, Bull. Soc. Chimique de France 1207, 1977.

Primary Examiner—Donald G. Daus
Assistant Examiner—William A. Teoli, Jr.
Attorney, Agent, or Firm—Ostrolenk, Faber, Gerb & Soffen

[57] ABSTRACT

The present invention is concerned with derivatives of 2,3,3a,4,5,6-hexahydro-1H-indolo(3,2,1-de)(1,5)naphthyridine of the formula

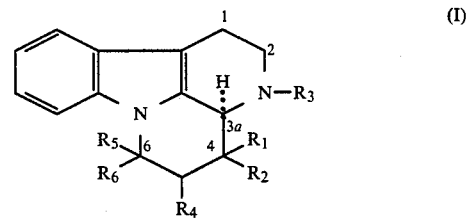

(I)

in the form of base or acid addition salts, preferably with pharmaceutically acceptable acids, wherein one of the groups R1 and R2 represents a lower alkyl group and the other represents a hydrogen atom or R1 and R2 represent each independently an alkyl group or, together an alkanediyl group having from 4 to 6 carbon atoms. R3 represents a lower alkyl group, a hydrogen atom or a benzyl group. And either R5 represents a lower carboalkoxy group or a hydrogen atom and R6 represents with R4 an additional carbon-carbon bond; or R4 represents a hydrogen atom and R6 and R5 represent together an oxygen atom or respectively a hydrogen atom and a hydroxyl group.

13 Claims, No Drawings

4-ALKYLINDOLONAPHTHYRIDINES AND THEIR THERAPEUTICAL APPLICATION

SUMMARY OF THE INVENTION

The present invention relates to new indolonaphthyridines substituted by one or two alkyl group at position 4 of the tetracyclic skeleton, to their method of preparation and to their therapeutical application.

These compounds may be used for treatment of cerebrovascular deficiencies, more particularly in geriatry.

The present invention is more particularly concerned with derivatives of 2,3,3a,4,5,6-hexahydro-1H-indolo(3,2,1-de)(1,5)naphthyridine of the formula

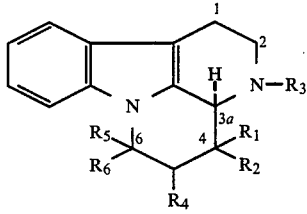

in the form of base or acid addition salts, preferably with pharmaceutically acceptable acids, wherein one of the groups R1 and R2 represents a lower alkyl group and the other represents a hydrogen atom or R1 and R2 represent each independently an alkyl group or, together, an alkanediyl group having from 4 to 6 carbon atoms, R3 represents a lower alkyl group, a hydrogen atom or a benzyl group and either R5 represents a lower carboalkoxy group or a hydrogen atom and R6 represents with R4 an additional carbon-carbon bond or R4 represents a hydrogen atom and R6 and R5 represent together an oxygen atom or respectively a hydrogen atom and a hydroxyl group.

BACKGROUND OF THE INVENTION

The polycylic skeleton of derivatives of the formula I may be compared with the one of vincamine wherein the cycle D is missing. This skeleton is identical to the one of canthin-6-ones which form a class of natural alcaloids (see for example L. A. Mitsher et al., Heterocyles, 3, 7, 1975).

We may thus described the compounds of the invention as derivatives of canthinones, canthinols or canthenes when, respectively, R5 and R6 represent in formula I an oxygen atom, R5 is a hydroxyl group and R6 a hydrogen atom or R6 represent a hydrogen atom and R4 and R5, together, is a additional C—C bond. The 1,2,3,3a,4,5-canthin-6-one skeleton corresponds to the 2,3,3a,4,5,6-hexahydro-6-oxo-1H-indolo(3,2,1-de)(1,5-)naphtyridine.

Belgian Pat. No. 853.435 discloses the preparation of a large number of differently substituted indolonaphthyridines. Among these, we may more particularly mention the 4-carboalkoxy-hexahydro-indolonaphthyridines.

Belgian Pat. No. 870.887 (U.S. Pat. No. 4,200,638) describes compounds of the formula I wherein R1=R2=H, R5 is a carbomethoxy group and R4 and R6 are together an additional carbon-carbon bond. They have been named chano-desethylapovincamines or "small apovincamines". Numerous similar derivatives are described in Belgian Pat. No. 884.145.

Belgian Pat. No. 857.816 (U.S. Pat. No. 4,218,453) describes and claims compounds of the formula I wherein R1 and R2 represent hydrogen atoms and R5 and R6 represent together an oxygen atom. These are also called hexahydrocanthin-6-ones derivatives. Belgian Pat. Nos. 816.759 and 882.024 describes the preparation of seco-D-homo-E-vincamones (also named chano-D-homovincamones) substituted at a position corresponding to the position 4 of formula I.

DETAILED DESCRIPTION OF THE INVENTION

It has now been found that more effective derivatives may be obtained by placing one or two lower alkyl substituents at position 4 of the 2,3,3a,4,5,6-hexahydro-1H-indolo (3,2,1-de)(1,5)naphthyridine.

These novel compounds are of formula I with the hereabovementionned significations for R1, R2, R3, R4, R5 and R6.

A lower alkyl group is understood to be a group having from 1 to 3 carbon atoms and a lower carboalkoxy group has 2 to 4 carbon atoms.

Each possible stereochemical forms of the compounds of formula I are included in the instant invention. In particular, these compounds may be present as optical stereoisomers or racemic mixture.

The preferred compounds are those wherein R1 and R2 represent each an ethyl group or R1 is an ethyl group and R2 is a hydrogen atom. Some more particularly preferred compounds in this group are:

3,4bêta-diethyl-1,2,3,3a,4,5-hexahydrocanthin-6-one and its optical isomer (I, R1=R3=ethyl, R2=R4=H, R5,R6=O), as a racemic mixture In methyl 3,4bêta-diethyl-2,3,3a,4-tetrahydro-1H-indolo (3,2,1-d,e) (1,5) naphthyridine-6-carboxylate (I, R1=R3=ethyl, R2=H, R4,R6=bond, R5=CO2CH3), as a racemic mixture Is.

3,4,4-triethyl-1,2,3,3a,4,5-canthin-6-one is also a compound showing remarkable pharmacological activity.

As far as the 4-substituted derivatives are concerned, it has been shown that generally one of the isomers at position 4 presents a more attractive pharmacological profile than the other. For the canthinones, on the basis of magnetic resonance spectra i.e. coupling constant, the stereochemistry H3a-H4 cis has been assigned to the more active isomer.

On the other hand a difference in polarity is usually observed between the isomers. For example the abovementioned derivative In, compared to its C-4 diastereoisomer is less polar as judging from the Rf in thin layer chromatography (ccm, silica gel, eluent dichloromethane:methanol 98:2) that is to say the Rf of In is higher.

In most cases, the compounds of the instant invention show reduced toxicities when compared with reference compounds such as vincamine and vincamone. There is also observed a remarkable and unexpected antianoxic activity associated with good hemodynamic and oxymetric activity. It has been shown than oral resorption problems, frequently arising with other active compounds from the prior art, are generally absent with the derivatives of the instant invention.

Several methods of preparation, some of them original, have been devised in order to prepare the derivatives described in the invention.

One of these methods is based on a condensation reaction of tryptamine with an aldehyde or a functionalised acid chloride (Pictet-Spengler or Bishler condensation), followed optionally by a classical chemical modification (dehydration, reduction etc . . . ). The functionalised aldehyde synthons have to be prepared accordingly (see for example compound 8 in Szantav et al, Heterocyles 6, 1149, 1977). These syntheses are similar to the ones described in Belgian Pat. Nos. 870,887 and 884,145 (U.S. Pat. No. 4,200,638).

In the particular case of derivatives of 4-ethyl-hexahydro-4-propyl-canthin-6-ones, compounds are obtainable by applying the Emde reaction starting from a dehydro-14,15-vincamone. Alkylation of the bêta-nitrogen of such a vincamone, followed by a catalytic hydrogenation results in the rupture of cycle D to afford the desired product. The alkylating agent is preferably methyl iodide or ethyl iodide and the catalyst may be platinum oxide.

Another synthetic pathway for canthinols and canthenes preparation involves a cycle regression of the corresponding homo-E derivatives of the formula:

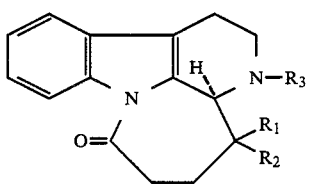

(II)

(see Belgian Pat. No. 816,759) via an intermediate of the formula:

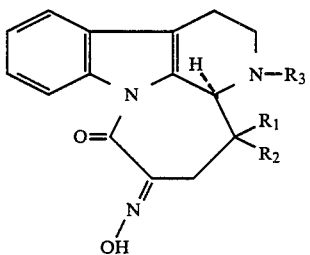

(III)

Cycle regression is achieved by oxidation of the homocanthinone II (a azepino(1,2,3-1,m)-bêta-carboline) to afford the corresponding oxyiminohomo-canthinone III.

This oxidation is carried out with an organic nitrite, for example t-butyl nitrite or isoamyl nitrite, in the presence of a base, preferably an alcoholate, in an inert organic solvent.

The oxo-hydroxyimino-canthane affords the corresponding canthinone through heating in a protic alhaline medium (for example NaOH-alcohol) for several hours, followed by acid treatment.

On the other hand, the corresponding "small vincamine" may thus be obtained from the oxo-hydroxyimino-canthane. For this purpose, the latter compound is heated, solubilized in, for example, a water-dioxanemethanol mixture, in the presence of sodium bisulfite or $NaHSO_3$. There is so provided both isomers at position 6 (alpha hydroxy, bêa hydroxy) which may be separated by recrystallization (see for Example Ir'a and Ir'b of Example 24).

It has also been observed that pyrrolo (2,3-d) carbazoles of the formula

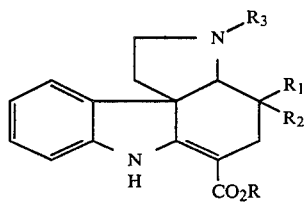

(IV)

are able, in the presence of an oxidation reagent in acid medium, to rearrange to afford the corresponding "small vincamines", that is to say derivatives of the formula I wherein $R_5$ and $R_6$ represent respectively a carboalkoxy group and a hydroxyl group and $R_4$ is a hydrogen atom.

This rearrangement is similar to the one observed with vincadifformine and which leads with excellent yields to vincamine (see Belgian Pat. Nos. 848,475 and 761,628, U.S. Pat. No. 3,892,755). The oxidant which is used to initiate the rearrangement is preferably an organic peracid as metachloroperbenzoic acid. Other peracids may be used, for example permaleic or perphthalic acids. The oxidation reagent may also be hydrogen peroxide, possibly in the presence of a metal catalyst such as copper or molybdenum-based catalysts.

"Small vincamines" provide after dehydration the corresponding "small apovincamines" which are an object of the invention. This is best achieved for example by azeotropic distillation in the presence of an acid catalyst such as paratoluenesulfonic acid. Certain classical "small vincamines" or "chanovincamines" have been described by Le Men et al, Bull. Soc. Chimique de France 1207, 1977.

Best yields for the abovementioned rearrangement have been obtained with derivatives disubstituted at position 4 of the pyrrolo(2,3-d)carbazole skeleton.

Pyrrolo(2,3-d)carbazole 6-carboxylates of formula IV or "seco-D-vincadifformines" are obtained starting from the corresponding azepino(4,5-b)indoles derivatives. The latter are described in the European patent application No. 64,317 (U.S. Pat. No. 4,362,739).

This synthetic pathway may also advantageously provide the corresponding "small vincamones" (hexahydrocanthinones), canthinols and canthenes. For this purpose, the "small vincamine" is reacted in the presence of an appropriate oxidizing reagent as described in the litterature for vincamine-type compounds (see for example Belgian Pat. No. 799,679—Richter).

The isolated hexahydrocanthinones may be reduced to provide the corresponding canthinols which in turn may be dehydrated to afford the corresponding canthenes.

Reduction is performed preferably with $LiAlH_4$ in THF at a temperature varying between $-10°$ C. and $0°$ C. Others metal hydrides may also be advantageously used. Dehydration is carried out in a classical way by azeotropic distillation in the presence of paratoluenesulfonic acid.

In the following examples, chemical shifts of NMR spectra are expressed in ppm relative to tetramethylsilane. Spectra have been run at 60 MHz. The following abbreviations are used: s=singlet, bs=broad singlet, m=multiplet, t=triplet.

Derivatives numbered with primes are diastereoisomers of the corresponding compounds without primes, isomerism arising from the relative position of the 4-ethyl and the 3a-hydrogen.

EXAMPLE 1

Methyl 3-benzyl-4,4-diethyl-1,2,3,3a,4,5-7H-pyrrolo(2,3-d)carbazole-6-carboxylate (seco-D-vincadifformine IVa)

(a) Methano-azepinoindole

A solution of 7 g of methyl 1,2,3,4,5,6-azepino(4,5-b)indole-5-carboxylate (28.6 mmol) and 3.43 g (34.3 mmol) of 2-ethylbutyraldehyde and 0.1 g of benzoic acid in 100 ml of $CH_3OH$ is stirred for 24 h at room temperature. There is thus isolated in a classical way around 10 g of methanoazepinoindole (see European patent application No. 64,317).

(b) Seco-D-vincadifformine IVa

A solution of methanoazepinoindole as obtained in (a), benzyl bromide (5.33 g, 31.1 mmol), diisopropylethylamine (7 mL) in 200 mL of $CHCl_3$ is refluxed for 6 days. After evaporation of the solvent, the residue is treated with 50 mL of $CH_3OH$, 200 mL of an aqueous saturated solution of $K_2CO_3$ and 200 mL of ether. The organic phase is separated. Aqueous phase is extracted three times with ether. The combined organic phases are washed (water) and dried. There is obtained 12.16 g or organic material which is purified by chromatographic separation on $SiO_2$ (eluent $CH_2Cl_2/2\%$ $CH_3OH$) and crystallization in $CH_3OH$. 9.86 g of compound IVa is isolated (yield: 83%).

Melting point: 111° C.

Mass spectrum: 416 (10%, M+), 332 (8), 202 (100), 91 (38)

Infrared spectrum (3%, $CCl_4$): 3385, 2964, 2880, 1680, 1621, 1610, 1462, 1435, 1247 $cm^{-1}$.

Ultraviolet spectrum ($CH_3OH$, max, nm, log $\epsilon$): 331 (4.26), 302 (4,08), 229 (4.03).

NMR spectrum ($CDCl_3$): 9.03 (bs, 1H), 7.70–6.60 (m, 9H), 4.33 (d, 1H, J=13 Hz), 3.93–3.46 (m, 4H), 3.23–1.33 (m, 9H)

EXAMPLE 2

Methyl 3-benzyl-4,4-diethyl-6-hydroxy-2,3,3,a4,5,6-hexahydro-1H-indolo(3,2,1-de)(1,5)naphthyridine-6-carboxylate Ia There is prepared a solution of 10 g (24 mmol) of seco-D-vincadifformine IVa in 225 mL of methanol containing 0.96 g HCl (pH=1). After addition of 4.84 g (24 mmol) and of 85% metachloroperbenzoic (MCPB), the reaction mixture is stirred for 3 h at room temperature. There is added 1.5 g of MCPB and stirring is continued for 10 h. $CH_3OH$ saturated with $NH_3$ is added to the solution until a basic pH is reached. After evaporation of the solvent, the residue is partitioned between 350 mL of $CH_2Cl_2$ and 150 mL of a saturated aqueous solution of $K_2CO_3$. The organic layer is separated. The aqueous phase is extracted twice with dichloromethane. The combined organic phases are washed with twice 200 mL of distilled water and 1×200 mL of a NaCl saturated aqueous solution. After drying over $Na_2SO_4$, filtration and evaporation, there is obtained 12.70 g of organic material which is purified by column chromatography on $SiO_2$ (eluent: $CH_2Cl_2$) and crystallization in methanol. There is so isolated 6.0 g of seco-D vincamine (only one isomer by tlc, yield 58%).

Melting point 151.5° C.

Ultraviolet spectrum: (max, $CH_3OH$): 276 nm

Infrared spectrum: ($CCl_4$, 3%) 3520, 3022, 2960, 2880, 1736, 1455, 1247 $cm^{-1}$.

NMR spectrum ($CDCl_3$): 7.53–6.76 (m, 9H), 4.30 (s, 1H), 4.00–3.56 (m, 4H), 3.13–1.90 (m, 6H), 1.15–0.60 (m, 6H).

EXAMPLE 3

Methyl 3-benzyl-4-spirocyclohexyl-6-hydroxy-2,3,3a,4,5,6-hexahydro-1H-indolo(3,2,1-de)(1,5)naphthyridine-6-carboxylate Ib There is prepared a suspension of 24.4 g (57 mmol) of the corresponding seco-D-vincadifformine IVb (see Example 22 of the European patent application No. 64,317) in 700 mL of $CH_3OH$ containing 0.5% HCl. MCPB (14.3 g, 0.07 mol) is added and the solution is stirred 2 h at room temperature. After adding $NH_3$ saturated methanol, the solution is concentrated under vacuum. The residue is treated with 300 mL of $CH_2Cl_2$ and 300 mL of an aqueous solution 1M in $Na_2CO_3$. The organic phase is decanted and separated and the aqueous phase is extracted twice with brine. The combined organic layers are further washed with distilled water and brine and dried over $Na_2SO_4$. After filtration and vacuum concentration, there is isolated 23 g of organic material. After crystallization in $CH_3OH$, there is obtained 11.33 g of the seco-D vincamine Ib. The mother liquor purified by chromatography on $SiO_2$ (eluent $CH_2Cl_2$) affords 1 g of additional Ib (total yield 49%).

Melting point 200° C.

Mass spectrum: 444 (16%, M+), 348 (10), 336 (59), 253 (51), 247 (66), 232 (15), 222 (26), 207 (20), 170 (35), 144 (61).

Ultraviolet spectrum ($CH_3OH$, max, nm): 276.

Infrared spectrum (KBr, 1%): 3500, 3030, 2935, 2860, 1737, 1459, 1437, 1242 $cm^{-1}$.

NMR spectrum ($CDCl_3$): 7.63–6.96 (m, 9H), 4.36 (s, 1H), 4.03–3.76 (m, 5H) with 3.86 (s, 3H), 3.43 (s, 1H), 3.16–1.06 (m, 16H).

EXAMPLE 4

Methyl 4,4-diethyl-6-hydroxy-2,3,3a,4,5,6-1H-indolo(3,2,1-de)(1,5)naphthyridine-6-carboxylate Ic Hydrogenation at atmospheric pressure of a solution of 9 g (20.8 mmol) of seco-D-vincamine Ia in 180 mL of acetic acid in the presence of 1.4 g of 10% charcoal-palladium is stopped after 15 h. The resulting solution is filtrated by decalite. The filter is rinsed with 80 mL methanol. The filtrated is poured into 300 mL of $CH_2Cl_2$ and alkalanised by dropwise addition of a saturated aqueous solution of $K_2CO_3$. The organic phase is separated and the aqueous phase extracted twice with $CH_2Cl_2$. The combined organic layers are washed with water then brine. After drying over $Na_2SO_4$, filtration and vacuum concentration, there is obtained 7.2 g of a white powder which affords, after crystallization from $CH_3OH$, 6.5 g of seco-D-vincamine Ic (yield 91.3%).

Melting point 174°–176° C.

Mass spectrum: 342 (49%, M+), 313 (13), 258 (18), 198 (24), 170 (100).

Infrared spectrum ($CHCl_3$): 3520, 2958, 1731, 1453, 1250 $cm^{-1}$.

Ultraviolet spectrum (nm, log): 281 (3.91).

NMR spectrum (CDCl$_3$): 7.46–6.80 (m, 4H), 4.53 (bs, 1H), 3.93 (s, 1H), 3.76 (s, 3H), 3.60–2.36 (m, 5H), 2.10 (d, 2H), 1.90–0.56 (m, 10H).

EXAMPLE 5

Methyl 4-spirocyclohexyl-2,3,3a,4,5,6-hexahydro-6-hydroxy-1H-indolo(3,2,1-de)naphthyridine-6-carboxylate Id Hydrogenation at atmospheric pressure of a solution comprising 6.66 g of seco-D-vincamine Ib (15 mmol) and 140 mL glacial acetic acid in the presence of 1.20 g of 10% palladium charcoal is stopped after 20 h. The solution is filtrated over decalite and the filter washed with 50 mL of methanol. The filtrate is poured into 250 mL of CH$_2$Cl$_2$ and alkalinised by stepwise addition of a saturated K$_2$CO$_3$ aqueous solution. The organic layer is decanted and the aqueous phase extracted twice with CH$_2$Cl$_2$. Combined organic phases are washed with water and brine. After drying over sodium sulfate, filtration, concentration under reduced pressure, there is obtained 5.39 g of a powder which provides, after crystallization in CH$_3$OH, 4.33 g of the seco-vincamine Id (yield 81.5%).

Melting point: 232°–235° C. (decomposition).

Ultraviolet spectrum (CH$_3$OH, log ε): 281 nm (3.93).

Infrared spectrum (KBr 1%): 3450, 2940, 1740, 1452, 1428, 1198 cm$^{-1}$.

Mass spectrum: 354 (98%, M+), 336 (10), 325 (27), 295 (15), 266 (17), 252 (27), 198 (28), 170 (100).

NMR spectrum (CDCl$_3$): 7.63–6.90 (m, 4H), 3.81 (s, 3H), 3.70 (m, 1H), 3.56–2.46 (m, 5H), 130–1.03 (m, 12H).

EXAMPLE 6

Methyl 4,4-diethyl-2,3,3a,4-tetrahydro-1H-indolo(3,2,1-de)(1,5-)naphthyridine-6-carboxylate Ie A suspension of 6 g (17.5 mmol) of seco-D-vincamine Ic and 6 g of paratoluenesulfonic acid (34.8 mmol) in 650 mL of dry benzene is refluxed in a 1 L flask equipped with a Dean-Stark separator. After 5 h of reflux, the cooled solution is poured into 300 mL of a 1M Na$_2$CO$_3$ aqueous solution. After stirring for 15 min, the mixture is decanted. The aqueous phase is extracted by 3×100 mL of benzene. The combined organic phases are washed with water then brine. After drying and evaporation under reduced pressure, there is obtained 5.95 g of organic residue. Crystallization in methanol affords 5.65 g of seco-D-apovincamine Ie (yield: 99%).

Melting point: 99° C.

Mass spectrum: 324 (100%, M+), 309 (83), 295 (30), 280 (7), 266 (14), 170 (54) for C$_{20}$H$_{24}$N$_2$O$_2$.

Infrared spectrum (CCl$_4$, 3%) 2960, 1734, 1738, 1609, 1453, 1440, 1253 cm$^{-1}$.

Ultraviolet spectrum (CH$_3$OH, 10 mg/L, max, nm, log ε): 275 (4.03), 313 (3.73).

NMR spectrum (CDCl$_3$): 7.63–6.86 (m, 4H), 6.10 (s, 1H), 4.15 (m, 1H), 3.93 (s, 1H), 3.6–2.53 (m, 4H), 1.93–0.36 (m, 11H) with 0.58 (t) and 1.00 (t).

EXAMPLE 7

Methyl 4-spirocyclohexyl-2,3,3a,4-1H-indolo(3,2,1-de)(1,5-)naphthyridine-6-carboxylate If.

A suspension of 7.83 g of seco-D-vincamine Id (22.1 mmol), 7.80 g of paratoluenesulfonic acid (41 mmol) in 850 mL benzene is refluxed for 5 h in a flask equipped with a Dean-Stark separator. The resulting solution, after cooling, is poured into 400 mL of a 1M Na$_2$CO$_3$ aqueous solution. After stirring for 30 min, the organic phase is separated and the aqueous phase extracted 3× with 100 mL of benzene. The combined organic phase are washed with water, then with saturated brine. After drying over sodium sulfate, filtration, evaporation and crystallization in methanol, there is isolated 6.77 g of seco-D-apovincamine If (yield 91%).

Melting point: 132°–134° C.

Infrared spectrum (KBr 1%): 3440, 2932, 2923, 2858, 1727, 1643, 1604, 1450, 1295, 1253 cm$^{-1}$.

Ultraviolet spectrum (CH$_3$OH, max, log ε): 315 (3.75), 275 (4.06).

NMR spectrum (CDCl$_3$): 7.53–6.86 (m, 4H), 6.45 (s, 1H), 3.90 (s, 3H), 3.73 (m, 1H), 3.51, 2.46 (m, 4H), 1.96–0.70 (m, 11H).

EXAMPLE 8

Methyl 3,4,4-triéthyl-2,3,3a,4-tetrahydro-1H-indolo(3,2,1-de)(1,5)naphthyridine-6-carboxylate Ig A suspension of 6 g (18.4 mmol) of seco-D-apovincamine Ie, 3.91 g Na$_2$CO$_3$ and 8.61 g ethyl iodide (55.2 mmol) in 150 mL of ethylmethylketone is refluxed for 24 h. After addition of 3 g of additional ethyl iodide, reflux is further continued for 24 h. After cooling, the reaction mixture is filtrate then concentrated in vacuo. The residue is distributed between 200 mL ether and 100 mL water. The aqueous phase is decanted and extracted twice with ether. The combined organic phases are washed with H$_2$O and sat NaCl. After drying and removal of the solvent, there is obtained 8 g of organic material which is purified by column chromatography on SiO$_2$ (elution CH$_2$Cl$_2$), then recrystallized from methanol. There is so obtained 4.5 g of the seco-D-apovincamine Ig homogeneous in tlc (yield 69.5%).

Melting point 73°–75° C.

Mass spectrum: 352 (M+, 100%), 337 (99), 323 (10), 198 (68) for C$_{22}$H$_{28}$N$_2$O$_2$.

Infrared spectrum (CCl$_4$, 3%): 2973, 1731, 1632, 1608, 1453, 1252, 1197 cm$^{-1}$.

Ultraviolet spectrum (CH$_3$OH, max, log ε): 274 (4.07), 313 (3.75) nm.

NMR spectrum (CDCl$_3$): 7.53–6.83 (m, 4H), 6.06 (s, 1H), 3.90 (s, 3H), 3.63 (bs, 1H), 3.33–2.30 (m, 6H), 1.66 (t, 3H), 1.13 (t, 3H), 0.56 (t, 3H).

EXAMPLE 9

Methyl 3-ethyl-4-spirocyclohexyl-2,3,3a,4-tetrahydro-1H-indolo(3,2,1-de)naphthyridine-6-carboxylate Ih Following the experimental procedure of the foregoing example, starting from If there is provided compound Ih.

Mass spectrum: 364 (M+, 30%) for C23 H28 N2 O2.

Infrared spectrum (KBr, 1%): 2937, 1730, 1633, 1600, 1490 cm$^{-1}$.

Ultraviolet spectrum: (CH$_3$OH, max): 270, 315 nm.

NMR spectrum (CDCl$_3$): 7.46–6.36 (m, 4H), 6.43 (s, 1H), 3.30 (s, 3H), 3.26 (bs, 1H), 3.13–2?56 (m, 6H), 2.00–0.76 (m, 13H).

EXAMPLE 10

3-benzyl-4,4-diethyl-1,2,3,3a,4,5-6H-canthinone-6 Ii

A suspension of 13.82 g (32 mmol) of the seco-D-vincamine Ia in 375 mL of a 0.28M KOH aqueous solution is refluxed for 5 h. The solution is cooled to +/− 10° C. and filtered through decalite. The filter is rinsed with 70 mL water. After addition of 23.5 g of $K_3Fe(CN)_6$), the aqueous solution is stirred at room temperature for 48 h. There is added 500 mL water and 500 mL $CH_2Cl_2$. The combined organic phases are washed with water then with saturated brine. After drying, filtration and in vacuo removal of the solvent, there is obtained a powder which is recrystallized from methanol to afford 9.80 g of hexahydrocanthinone Ii (yield: 82%).

Melting point 172.6° C.

Ultraviolet spectrum ($CH_3OH$, max, log $\epsilon$): 305 (3.88), 266 (4.16), 241 (4.46).

Infrared spectrum (KBr, 1%): 2964, 1704, 1632, 1456, 1370, 1334, 1140 cm$^{-1}$.

NMR spectrum ($CDCl_3$): 8.40 (1H, m), 3.93 (s, 2H), 3.76 (s, 1H), 3.26–2.16 (m, 6H), 2.03–0.53 (m, 10H).

EXAMPLE 11

4,4-diethyl-1,2,3,3a,4,5-canthin-6-one Ij

Hydrogenation at atmospheric pressure of a solution of 1.5 g (4.03 mmol) hexahydrocanthinone Ii (Example 10) in 40 mL of glacial acetic acid in 5 mL of $CH_3OH$—HCl 3%, in the presence of 0.4 g 10% Pd on charcoal is stopped after 5 h. After adding 10 mL of $CH_3OH$, the solution is heated until dissolution of the formed precipitate. The solution is hot filtrated through decalite. The filter is washed with methanol. The solvent is removed under reduced pressure. The residue is distributed between 50 mL of $CH_2Cl_2$ and 50 mL of a $K_2CO_3$ saturated aqueous solution. After stirring for 15 min, the phases are separated. The aqueous phase is extracted twice with $CH_2Cl_2$. The combined organic phases are washed with water and saturated brine, then dried over sodium sulfate. After filtration and removal of the solvent, there is obtained 1.00 g of organic material which affords after crystallization from methanol 0.9 g of pure canthinone Ij (yield: 79%).

Melting point: 113° C.

UV spectrum ($CH_3OH$): 295 (3.66), 268 (4.01), 242 (4.30).

IR spectrum (3% $CCl_4$): 3055, 2970, 1708, 1630, 1450, 1376, 1332, 1133 cm$^{-1}$.

NMR spectrum ($CDCl_3$): 8.26 (m, 1H), 7.40–6.96 (m, 3H), 3.86 (m, 1H), 3.63–2.33 (m, 7H) whrein 2.50 (s, 2H), 1.73–0.50 (m, 10H).

EXAMPLE 12

3,4,4-triethyl-1,2,3,3a,4,5-hexahydrocanthin-6-one Ik

A solution of 26.5 g (94 mmol) canthinone Ij and 73.2 g (0.469 mol) ethyl iodide in 350 mL of ethylmethylketone containing 19.92 g $Na_2CO_3$ is refluxed for 5 days. The solvent is removed in vacuo and the residue is partitioned between 300 mL of $CH_2Cl_2$ and 200 mL of distilled water. The organic phase is washed with NaCl saturated water and dried over magnesium sulfate. After removal of the solvent, the residue is purified by column chromatography on $SiO_2$ (eluent $CH_2Cl_2$:$CH_3OH$ 98.5:1.5) to yield 21 g of Ik as an amorphous oil (72%).

Melting point (hydrochloride): 197°–200° C. (decomposition).

Mass spectrum: 310 (M+, 70), 281 (44), 198 (100) for $C_{20}H_{25}N_2O$.

Ultraviolet spectrum ($CH_3OH$) 242, 267, 295.

Infrared spectrum (3%, $CCl_4$): 2968, 1709, 1624, 1453, 1364, 1330 cm)$^{-1}$.

NMR spectrum ($CDCl_3$): 8.20 (m, 1H), 7.40–6.93 (m, 3H), 3.46 (bs, 1H), 3.21–2.16 (m, 8H) wherein 2.45 (s, 2H), 1.73–0.50 (m).

EXAMPLE 13

3-ethyl-1,2,3,3a,4,5-hexahydro-4-spirocyclohexyl-canthin-6-one II

Following a procedure similar to the one of examples 10, 11 and 12, but starting from Id, compound II is prepared.

Melting point: 144.8° C.

Mass spectrum: 322 (M+) for $C_{21}H_{26}N_2O$.

Infrared spectrum (1% KBr): 2970, 2935, 2860, 1703, 1622, 1453, 1380 cm$^{-1}$.

Ultraviolet spectrum ($CH_3OH$): 243, 266, 293 nm.

NMR spectrum ($CDCl_3$): 8.26 (m, 1H), 7.56–7.00 (m, 3H), 3.26 (1H), 3.20–2.33 (m, 8H), 2.03–0.86 (m, 13H).

EXAMPLE 14

3,4-diethyl-1,2,3,3a,4,5,6,7-octahydro-7-oxo-6-oxyimino-azepino(1,2,3-Im)-β-carboline III 64.9 mL of tert-butylnitrite (0.56 mol) is added to a solution of 15 g (0.05 mol) chano-E-homovincamone II (more polar isomer R1=R3=ethyl, R2=H, see Belgian Pat. No. 882.024) in 300 mL of dry toluene. There is then added a solution of 82.8 mmol of sodium tert-amylate in 150 mL of toluene. The resulting reaction mixture is stirred for 90 min. The latter is then poured into 500 mL of an aqueous solution containing 10% ammonium chloride and the organic phase is separated and washed with water, dried over magnesium sulfate and evaporated to dryness. A resulting solid residue (16 g), homogeneous by tlc on $SiO_2$, is so obtained. The hydrochloride is prepared by dissolving this material in acetone followed by addition of ether—HCl until an acid pH is reached. There is thus obtained 11 g of white crystals.

Melting point (hydrochloride): 236° C.

Mass spectrum (m/e): 325, 308, 296, 283, 268, 252, 239, 226, 214, 199, 198, 180, 167 for $C_{19}H_{23}N_3O_2$.

Ultraviolet spectrum (hydrochloride), c=2.73.10$^{-5}$ mol/L, $CH_3OH$, max, log $\epsilon$): 257 (4.26), 308 (3.69) nm.

Infrared spectrum (base, film): 3400, 2970, 1685, 1610, 1450, 1370, 1330, 910, 730.

NMR spectrum (base, $CDCl_3$): 8.4 (massif, 1H), 7.4–7.0 (m, 3H), 3.9 (d, 1H, J 3a–4:5 cps), 1.3–0.8 (m, 6H).

EXAMPLE 15

3,4-diethyl-2,3,3a,4,5,6-hexahydro-6-oxo-1H-indolo(3,2,1-de)(1,5)-naphthyridine In 9.45 g (29 mmol) of 3,4-diethyl-1,2,3,3a,4,5,6,7-octahydro-7-oxo-6-oxyimino-azepino(1,2,3-Im)-carboline is treated by 40 mL of ethoxyethanol (as a suspension). There is added 2.32 g (58 mmol) of NaOH and the reaction mixture is stirred for 1 h at room temperature then refluxed for 18 h. The reaction mixture is then evaporated to dryness and the residue taken up with 50 mL 3N HCl and further refluxed for 1 h. The solution is cooled, made alkaline and extracted with $CH_2Cl_2$. The separated organic phase is stirred for 15 min in the presence of 100 g of $Al_2O_3$. After filtration of the alumina, the filtrate is washed with water, dried and concentrated to dryness. There is so obtained 6 g of a solid residue which is dissolved in acetone in order to prepare the corresponding hydrochloride by stepwise addition of HCl saturated ether. Filtration affords 4 g of white crystals.

Compound In is less polar as assessed by tlc Rf when it is compared with its isomer at position 4 (see compound In' Example 21 infra).

Melting point (hydrochloride): 240°–241° C.

Mass spectrum (m/e): 282, 281, 267, 253, 225, 198, 197, 196, 182, 167, 154, 142 for $C_{18}H_{22}N_2O$.

Ultraviolet spectrum (hydrochloride, c=3.14 $10^{-5}$ mol/L, $CH_3OH$, max, log 242 (4.29), 2.65 (3.99), 298–303 (3.59).

Infrared spectrum (base, film): 2960, 1700, 1635, 1450, 1380, 1320, 1150, 910, 750.

NMR spectrum ($CDCl_3$): 8.3 (m, 1H), 7.4–7.1 (m, 3H), 1.3–0.8 (m, 6H).

EXAMPLE 16

3,4-diethyl-2,3,3a,4,5,6-hexahydro-6-hydroxy-1H-indolo (3,2,1-de) (1,5) naphthyridine Io (canthinol)

2.61 g (69 mmol) of $LiAlH_4$ is placed in suspension in 86 mL tetrahydrofuran (THF) and the resulting mixture is cooled to −5° C. A solution (14.54 g, 51 mmol) of 3,4-diethyl-2,3,3a,4,5,6-hexahydro-6-oxo-1H indolo(3,2,1-de)(1,5)naphthyridine In in 190 mL dry THF is then added dropwise, avoiding a rise of temperature above 0° C. 30 min after the end of the addition, $LiAlH_4$ excess is destroyed by slow addition of wet THF. Salts are filtrated off through decalite and the filtrate is concentrated in vacuo to dryness. The residue is treated by $CH_2Cl_2$ and extracted by a 2% $H_2SO_4$ solution. The acidic aqueous phase is washed, dried and evaporated and the resulting residue is crystallized from acetone to afford 12 g (42 mmol) of a tlc homogeneous product ($SiO_2$, $CH_2Cl_2$-5% $CH_3OH$). Yield: 82%.

Melting point: 176°–178° C.

Mass spectrum: 284 (M+) for $C_{18}H_{24}N_2O$.

Ultraviolet spectrum (c=3.54 $10^{-5}$ mol/L, $CH_3OH$, log): 228 (4.52), 2.81 (3.86), 290 (shoulder, 3.74) nm.

Infrared spectrum (KBr): 3200, 2800, 1460, 1190, 1050, 740.

NMR spectrum (base, DMSO-d6): 7.6–6.9 (m, 4H), 6.3 (m, 1H), 6.00 (1H, 1.3–0.9 (m, 6H).

EXAMPLE 17

3,4-diethyl-2,3,3a,4-tetrahyro-1H-indolo (3,2,1-de)(1,5) naphthyridine Ip (canthene)

5.85 g (20 mmol) 3,4-diethyl-2,3,3a,4,5,6-hexahydro-6-hydroxy-1H-indolo (3,2,1-de) (1,5) naphtyridine Io and 0.5 g (3.1 mmol) of paratoluenesulfonic acid monohydrate are dissolved in 160 mL of toluene and reluxed through a Dean-Stark water separator. After refluxing for 30 min, the reaction mixture is cooled, diluted with 150 mL of $CH_2Cl_2$ and stirred with 60 g of $Al_2O_3$ for 10 min. The mixture is filtrated and the filtrate is concentrated to half its original volume, then washed with water, dried, and evaporated in vacuo. The residue is treated by acetone and the hydrochloride is obtained by dropwise addition of HCl-ethanol, until a pH 6 is reached. The resulting white crystals are filtrated, washed with acetone and dried under vacuum. There is so obtained 4.37 g of the hydrochloride of Io.

Melting point (hydrochloride): 204°–205° C.

Mass spectrum: 266 (M+) for $C_{18}H_{22}N_2$.

Ultraviolet spectrum (hydrochloride, c=3.32 $10^{-5}$ mol/L, $CH_3OH$, max, log ε): 221 (4.40), 257 (4.43), 301 (3.86), 310 (3.87) nm.

Infrared spectrum (film): 2800, 1640, 1450, 1400, 1310, 1070, 910, 740 cm$^{-1}$.

NMR spectrum ($CDCl_3$) 7.5–6.9 (m, 4H), 6.8 (d, 1H J5–6=8 cps), 5.2 (d×d J 5–6=8 cps, J 5–4=7 cps), 3.4 (d, 1H, J 3a–4=6 cps), 1.3–0.7 (m, 6H).

EXAIMPLE 18

Methyl 3,4-diethyl-2,3,3a,4,5,6-hexahydro-hydroxy-6 1H indolo (3,2,1-de)(1,5) naphthyridine-6-carboxylate Ir 10 g (30 mmol) of 3,4-diethyl-1,2,3,3a,4,5,6,7-octahydro-oxo-7 oxyimino-6 azepino (1,2,3-Im)-carboline is put in suspension in a mixture of 200 mL water, 100 mL methanol and 100 mL dioxane. There is added 9.4 g (90 mmol) of $NaHSO_3$ and reflux is initiated. After 6 h, 9.4 g of additional $NaHSO_3$ is added and the reflux is continued for 16 h. The reaction mixture is then cooled, diluted with 200 mL water, rendered alkaline by addition of $NH_4OH$, and extracted with $CH_2Cl_2$. The organic layer is separated and extracted with 2% sulfuric acid. The acid aqueous phase is eventually made basic and extracted with $CH_2Cl_2$. The combined $CH_2Cl_2$ phases are washed, dried and evaporated to dryness. There is so obtained 2 isomers Ir(a) and Ir(b), a "small vincamine" and the corresponding "small isovincamine", which may be directly used for the procedure of the following example. However, this mixture being dissolved in acetone and HCl satured methanol added, the less polar isomer Ir(a) crystallizes and is isolated after usual work-up.

Melting point (hydrochloride): 213° C.

Mass spectrum: 342 (M+) for $C_{20}H_{26}N_2O_3$.

Infrared spectrum (KBr): 3300, 2960, 2550, 1740, 1460, 1230, 750 cm$^{-1}$.

Ultraviolet spectrum (c=2.64 $10^{-5}$ mol/L, $CH_3OH$, max, log): 225 (4.5), 272 (3.91), 275–279 (3.90), 288–290 (3.75) nm.

EXAMPLE 19

Methyl 3,4-diethyl-2,3,3a,4-tetrahydro-1H-indol (3,2,1-de) (1,5) naphthyridine-6-carboxylate Is A mixture of both isomers of methyl 3,4-diethyl-2,3,,3a,4,5,6-hexahydro-6-hydroxy 1H indolo (3,2,1-de) (1,5)naphtyridine-6-carboxylate (4.28 g, 12.5 mmol) is dissolved in 100 mL of 1,2-dichloroethane. 7.13 g (37.5 mmol) paratoluenesulfonic acid monohydrate is added and the azeotrope is distilled off. When the reaction mixture temperature reaches 82° C., the solution is cooled. There is added 100 mL of $CH_2Cl_2$ and the resulting solution is washed with aqueous $NH_4OH$ then water. The organic phase is stirred in presence of 25 g $Al_2O_3$. After filtration, the solution is washed, dried and vacuum evaporated to yield 3.7 g of the desired product. The latter is transformed into the corresponding hydrochloride by dissolving in acetone and treatment with gaseous HCl until an acid pH is observed. Crystals are filtrated, washed with acetone and dried.

Melting point (hydrochloride): 219°–220° C.

Mass spectrum (m/e): 324, 309, 295, 282, 269, 252, 238, 219, 198, 183, 169, 142.

Ultraviolet spectrum (hydrochloride, c=2.76 $10^{-5}$ mol/L, $CH_3OH$, max, log ε): 228 (4.51), 2.74 (4.04), 314 (3.73) nm.

Infrared spectrum (base, film): 2960, 1725, 1640, 1610, 1450, 1280, 1260, 910, 740.

NMR spectrum (base, CDCl$_3$): 7.5–6.9 (m, 4H), 6.4 (d, 1H), 3.9 (s, 3H), 3.5 (d, J=5 cps), 1.1 (t, 3H), 0.75 (m, 3H).

EXAMPLE 20

3,4-diethyl-1,2,3,3a,4,5,6,7-octahydro-7-oxo-6 oxyimino azepino (1,2,3-Im)-β-carboline III'

Following the procedure of example 14, but starting from 13.5 g of II wherein R1=R3=ethyl and R2=H (less polar isomer judging by tlc Rf), there is obtained 12.3 g of the corresponding oxyimino derivative III'.

Melting point (hydrochloride): 264°–265° C.

Mass spectrum (m/e): 325, 308, 296, 282, 268, 251, 226, 199, 198, 197, 169 for C$_{19}$H$_{23}$N$_3$O$_2$.

Ultraviolet spectrum (hydrochloride, c=5.33 10$^{-5}$ mol/L, CH$_3$OH, max, log ε): 258 (4.16), 313 (3.71) nm Infrared spectrum (film): 3400, 2960, 1680, 1610, 1450, 1380, 1330, 1020, 750, 730.

NMR spectrum (base, CDCl$_3$): 8.4 (m, 1H), 7.4–7.0 (m, 3H), 3.5 (d, 1H, J 3a-11 cps), 1.3–0.9 (m, 6H).

EXAMPLE 21

3,4-diethyl-2,3,3a,4,5,6-hexahydro-6-oxo-1H-indolo (3,2,1-de)(1,5) naphthyridine In'

Following a procedure similar to the one of example 16 but starting from 9.56 g of III' there is recovered 4.17 g of derivative In'.

The latter is more polar judging by its tlc Rf when compared with its diastereoisomer In of Example 15.

Melting point (hydrochloride): 242°–243° C.

Mass spectrum (m/e): 282, 281, 267, 253, 239, 226, 199, 198, 197, 196, 168 for C$_{18}$H$_{22}$N$_2$O.

Ultraviolet spectrum (hydrochloride, c=3.13 10$^{-5}$ mol/L, CH$_3$OH, max, log 242 (4.30), 266 (4.00), 297–305 (3.59).

Infrared spectrum (film, base): 2970, 1700, 1630, 1450, 1380, 1330, 1140, 910, 740 cm$^{-1}$.

NMR spectrum (base, CDCl$_3$): 8.4 (m, 1H), 7.4–7.1 (m, 3H), 3.7 (d 1H: J3A-4=10 cps), 1.3–0.8 (m, 6H).

EXAMPLE 22

3,4-diethyl-2,3,3a,4,5,6-hexahydro-6-hydroxy 1H-indolo (3,2,1-de) (1,5) naphthyridine Io'

Using an experimental procedure similar to the one of example 17 there is afforded Io' with a yield of 85%.

Melting point: 129°–130° C.

Mass spectrum: 284 (M+) for C$_{18}$H$_{24}$N$_2$O.

Infrared spectrum (base, KBr): 3350, 2920, 1420, 1250, 1170, 1025, 720 cm$^{-1}$.

Ultraviolet spectrum (base, c=3.15 10$^{-5}$ mol/L, CH$_3$OH, max, log ε): 228 (4.52), 275–282 (4.02), 290 (shoulder, 3.78)

NMR spectrum (CDCl$_3$+CD$_3$OD): 7.4–6.9 (m, 4H), 5.8 (m, 1H), 1.3–0.8 (m, 6H).

EXAMPLE 23

3,4-diethyl-1,2,3,3a-tetrahydro-indolo (3,2,1-de) (1,5) naphthyridine Ip'

Following a procedure similar to the one of example 18 Ip' is obtained with a yield of 69%.

Melting point (hydrochloride) 199°–201° C.

Mass spectrum (m/e): 266, 251, 237, 221, 208, 194, 180, 167, 133 for C$_{18}$H$_{22}$N$_2$.

Infrared spectrum (base, film): 2960, 1670, 1460, 1430, 910, 740 cm$^{-1}$.

Ultraviolet spectrum (hydrochloride, c=3.31 10$^{-5}$ mol/L, max, log ε): 221 (4.40), 257 (4.45), 301 (3.89), 310 (3.89).

NMR spectrum (base, CDCl$_3$): 7.6–7.0 (m, 4H), 6.8 (1H, d×d, J5-6=8 cps J5-6=2 cps), 3.8 (d, J3a-4=12 cps), 1.2–0.8 (m, 6H).

EXAMPLE 24

Methyl 3,4-diethyl-2,3,3a,4,5,6-hexahydro-6-hydroxy 1H indolo (3,2,1-de)(1,5) naphthyridine-6-carboxylate Ir'(a and b)

11 g (33.8 mmol) of 3,4-diethyl-1,2,3,3a,4,5,6,7-7-oxo 6-oxyimino azepino (1,2,3-Im)-β-carboline (example 20) is added to 20 mL of water, 100 mL of CH$_3$OH and 100 mL of dioxane. There is further added 17 g (0.14 mol) of NaHSO$_3$ and the resulting suspension is refluxed. After 5 h, an additional 17 g of NaHSO$_3$ is added and reflux is continued for 16 h. The reaction mixture is then cooled, made basic and extracted with CH$_2$Cl$_2$. The CH$_2$Cl$_2$ phase is extracted with 2% sulfuric acid and the aqueous phase is separated and made basic by addition of 10% NH$_4$OH, then extracted with CH$_2$Cl$_2$. The organic layer is washed, dried and evaporated in vacuo. There is thus obtained 4 g of a mixture of 2 isomers under the form of a yellow solid which may be directly used in the following steps of synthesis. These isomers at position 6 ("small vincamine" and "small isovincamine") may however be isolated and further purified by successive recrystallisations from a mixture of acetone, ethyl acetate and diethylether. The hydrochloride of each isomers may be obtained by dissolving in acetone and treating with HCl saturated methanol.

Physico-chemical properties of the less polar isomer Ir'(a)

Melting point (base) 187° C.

Mass spectrum: 342 (M+) for C$_{20}$H$_{26}$N$_2$O$_3$.

Ultraviolet spectrum (base, c=2.97 10$^{-5}$ mol/L, CH$_3$OH), max, log ε): 226 (4.55), 276–280 (3.92), 288 (shoulder) nm.

Infrared spectrum (base, KBr): 2940, 1740, 1460, 1260, 1220, 1060, 750 cm$^{-1}$ NMR spectrum (base, CDCl$_3$+CD$_3$OH): 7.4–6.8 (m, 4H), 3.8 (s, 3H), 1.3–0.9 (m, 6H).

Physicochemical properties of the more polar isomer Ir'(b)

Melting point (hydrochloride): 183° C.

Mass spectrum: 342 (M+) for C$_{20}$H$_{26}$N$_2$O$_3$.

Ultraviolet spectrum (hydrochloride, c=2.64 10$^{-5}$ mol/L, CH$_3$OH, max, log ε): 224 (4.41), 273 (3.79), 277–281 (3.77), 288–290 (3.59) nm.

Infrared spectrum (base, KBr): 3400, 2960, 1740, 1450, 1260, 1200, 1140, 1100, 750.

NMR spectrum (base, CDCl$_3$): 7.4–6.9 (m, 4H), 4.7 (m, 1H exchanges with D$_2$O), 3.6 (s, 3H), 1.2–0.8 (m, 6H).

EXAMPLE 25

Methyl 3,4-diethyl-2,3,3a,4-tetrahydro-1H-indolo (3,2,1-de)(1,5) naphthyridine-6-carboxylate I's 12.82 g (37.4 mmol) of a mixture of both isomers of methyl 3,4-diethyl-1,2,3,3a,4,5-6-hydroxy 1H indolo (3,2,1-de)(1,5) naphthyridine-6-carboxylate (Ir'(a) and Ir'(b) of Example 24) is dissolved in 30 mL of 1,2-dichloroethane. There is added 21.36 g (112 mmol) of paratoluenesulfonic acid monohydrate and the azeotrope is distilled off. When the temperature reaches 82° C., the reaction solution is cooled. There is added 300 mL of $CH_2Cl_2$ and the solution is washed with aqueous diluted $NH_4OH$ and distilled water. The organic layer is stirred in the presence of 64 g of $Al_2O_3$ and after filtration, the filtrate is washed, dried and concentrated to dryness. The residue is dissolved in 100 mL of acetone and gaseous HCl is bubbled to an acidic pH. The resulting crystals are filtrate, rinsed with acetone and dried. 10.9 g of white crystals is recovered.

Melting point (hydrochloride): 199°-200° C.

Mass spectrum (m/e): 324, 309, 307, 293, 238, 236, 180, 165, 127 for $C_{20}H_{24}N_2O_2$.

Ultraviolet spectrum (hydrochloride, $c=2.77 \cdot 10^{-5}$ mmol/L, $CH_3OH$): 244 (4.53), 269 (4.09), 313 (3.83) nm.

Infrared spectrum (film, base): 2970, 1725, 1630, 1450, 1230, 910, 740 $cm^{-1}$.

NMR spectrum (base, $CDCl_3$): 7.5-6.9 (m, 4H), 6.2 (d, 1H, J=2 cps), 3.9 (s, 3H), 3.6 (d, J=11 cps), 1.3-0.9 (m, 6H).

EXAMPLE 26

(−) 4-ethyl-1,2,3,3a,4,5-4-propyl canthin-6-one It (a) 10 g (34 mmol) of 14,15-dehydro vincamone is dissolved in 500 mL of methanol and there is added an excess of methyl iodide (18.75 mL, 42.8 g, 0.3 mol). The reaction mixture is stirred for 20 h until complete dissapearance of the dehydrovincamine as monitored by tlc. The solution is evaporated to dryness and the residual material recrystallise from $CH_2Cl_2$. A quaternary ammonium salt very polar in tlc is so isolated (7.18 g).

(b) 7.18 g of the said quaternary ammonium is put in suspension in $CH_3OH$ (115 mL) and 1.43 g of $PtO_2$ 80% is added after saturation of the reaction vessel with argon. The apparatus is placed under hydrogen pressure after removal of the inert gas. The resulting mixture is stirred for 20 h at atmospheric pressure. The theoretical quantity of hydrogen being absorbed, tlc analysis confirms the absence of polar product. The mixture is filtrated on decalite and the solvent is removed in vacuo. The residue is taken up with $CH_2Cl_2$ and treated with aqueous $NH_4OH$. The organic layer is washed twice with water, dried over magnesium sulfate and concentrated to dryness. There is so obtained 4.5 g hof a tlc homogeneous compound which may be recrystallized under the form of a hydrochloride from a HCl-acetone-diethylether solvent system.

Ultraviolet spectrum ($CH_3OH$, log ε): 242, 267, 294, 301 nm.

Infrared spectrum ($CHCl_3$): 3680, 3600, 2960, 2800, 1700, 1625, 1450, 1380, 1330 $cm^{-1}$.

NMR spectrum ($CDCl_3$): 2.63 (s, 3H), 3.5 (s, 1H), 7.3 (m, 3H), 8.3 (m, 1H).

Optical rotation: $a_D = -25.7°$ (c=0.894, $CHCl_3$).

As stated hereinabove, the instant invention comprises also the industrial applications of the disclosed compounds, more particularly the pharmaceutical applications. Compounds of the formula (I) have been tested and have been shown to possess very interesting pharmacological properties which render then susceptible of therapeutical applications for example as antianoxics, psychotropics and cerebral oxygenators.

Acute toxicities

Compounds of the invention have been injected (as hydrochlorides) intravenously to Charles River mice. Lethal doses (50% (DL50) have been graphically determined using the method of Lichtfield and Wilcoxon (J. Pharmacol. Exp. Therap. 1946, 96, 99).

Hypobaric hypoxia test in mice

Mice of identical sexes, of Charles River breed, weighting 20 g+/−2 g are distributed in 3 lots of 10 animals. Lots numbered 1 and 2 comprised treated animals, that is to say having received the tested substance as a hydrochloride. Third lot is for reference animals. Compounds are given 30 min before the anoxia test. The animals are placed in an atmosphere with reduced oxygen content. This is done by provoking a partial vacuum (190 mm Hg, corresponding to 5.25% oxygen), this low pressure being reached in 30 seconds. With a chronometer, the survival time of each animal is measured. Compounds capable of improving tissue oxygenation, more particularly cerebral oxygenation, cause increased survival time which may be expressed by the 50% active dose (AD50), that is to say the dose increasing mean survival time by 50% for animals placed in the abovementioned conditions.

Results obtained with some derivatives of the invention are collected in the following table:

| Compound | Example n° | Acute toxicities DL50 ig | iv | Hypobaric hypoxia AD50 | Coeff |
|---|---|---|---|---|---|
| Ig | 8 | >2000 | 82 | 117 | >17.9 |
| In' | 21 | 550 | 11 | | inactive |
| In | 15 | 1500 | 65 | 45 | 33 |
| Ik | 12 | 1425 | 70 | 40 | 35.6 |
| Ie | 6 | 545 | 32 | | |
| vincamine | | 1150 | 46 | 90 | 12.7 |
| vincamone | | 796 | 30 | 25 | 31.8 |
| Is | 19 | >2000 | | 92 | >22 |
| Ip | 17 | 860 | | 70 | 12.3 |
| Is' | 25 | 1585 | | 95 | 16.6 |
| Ip' | 23 | 220 | | 40 | 5.5 |

Compared to vincamine, at a dose corresponding to the same fraction of DL50, most compounds of the instant invention are more active in the test of hypobaric hypoxia. We may point the exceptional activity of compound In, in spite of its diastereisomer In' being inactive.

Compounds with the chemical structure of In, Is, and Ip without an ethyl group at position 4 of the formula I have coefficient LD50/DE50 hypobaric hypoxia (Coeff, in the table) respectively of 10.3, 5.5 and 12.3. Compounds of the invention may thus be compared advantageously with the structurally related ones described in the prior art.

(+/−) 3,4-diethyl-hexahydrocanthin-6-one In and the corresponding 6 carbomethoxy Is' exhibits also remarkable hemodynamic and oxymetric properties, as assessed from oxygen consumption derived from the $CMRO_2$ (cerebral metabolic rate of $O_2$).

Other pharmacological tests demonstrated the superiority of the compounds of the invention when compared with structurally related derivatives, more particularly derivatives without a 4-alkyl group in the indolonaphtyridine skeleton.

There has also been shown that the cardiotoxicity of, for example compounds In and Ig, is far less important when compared with clinically used analogs such as vincamine, vincamone and vinpocetine. Thus 20 mg iv of In in the rabbit is less cardiotoxic than 1 mg of vincamine.

On the other hand the test of the action again the oedema induced by triethyl-tin, that is to say inhibition of the swelling of brain tissue, (J. Path. Bact. 73, 107–123, 1957) has been shown to be particularly demonstrative for instance for compounds In, Lg, Is and Ip. Is is four times more effective compared to vincamine.

Compounds of the instant invention, having cumulative antianoxic and psychotropic activity, may be used in human therapy as cognitive activator or for the treatment of the vigilance insufficiencies, more particularly to act again troubles arising from comportement caused by impaired cerebral vessels circulation, cerebral sclerosa in geriatry, as sedative and also for the treatment of mental absences due to cranial traumatisms, and treatment of certain depressive states.

They are generally useful for treating cerebro-vascular and cardio-circulatory disorders.

For their therapeutical applications, compounds of the invention will be administered using the oral route in the form of capsules, tablets, solution syrups, powders or suspensions or using parenteral route under the form of buffered or not sterile solute, prepared in advance or extratemporaneously. The active substance in the form of a salt or a base is present at a dose of from 0.5 to 700 mg. Daily dosage may varied from 1 to 700 mg of active substance depending on the treatment and the host.

Compounds of the invention are thus present in the form of pharmaceutical preparations containing at least one of them as active components, alone or possible, in association with other active principles.

The usual excipents or pharmaceutically acceptable carriers such as starch, lactose, talc may be used. Pharmaceutical compositions may also contained anti-oxydants, preservatives, lubricating agents, binding, flavoring, sweetening or coloring agents etc. . . .

Salts more useful for the therapeutical application are salts derived from pharmaceutically acceptable acids well-known in pharmacy, more particularly the hydrochloric and methanesulfonic acid addition salts, which may be solvated, more particularly hydrated, to a certain extent.

I claim:

1. A 2,2,3,3a,4,5,6-hexahydro 1H indolo(3,2,1-de)(1,5-)naphtyridine of formula in the form of base or acid addition salt, wherein one of the groups R1 and R2 represents a $C_{2-3}$ alkyl group and the other represents a hydrogen atom in the cis configuration relative to the 3a hydrogen or R1 and R2 represent each independently an alkyl group or, together, an alkanediyl group having from 4 to 6 carbon atoms, R3 represents a lower alkyl group or a hydrogen atom and either R5 represents a lower carboalkoxy group or a hydrogen atom and R6 represents with R4 an additional carbon-carbon bond or R4 represents a hydrogen atom and R6 and R5 represent together an oxygen atom or respectively a hydrogen atom and a hydroxyl group.

2. Compound according to claim 1 wherein in formula I at least one of R1 and R2 represent an ethyl group.

3. Compound according to claim 1 wherein R1=R3=ethyl, R2=R4=H and R5 and R6 represent together an oxygen atom.

4. Compound according to claim 3 characterized in that it is the less polar isomer as assessed by thin layer chromatography on silica gel, the eluent being a mixture $CH_2Cl_2$—$CH_3OH$ (98:2, v:v).

5. Compound according to claim 1 or 2 wherein R1=H and R2=bêta-ethyl and its optical isomer.

6. (+/−) 3,4-diethyl-2,3,3a,4,5,6-hexahydro-6-oxo-1H-indolo (3,2,1-de) (1,5) naphthyridine and its addition salt with sulfuric acid.

7. Compound according to claim 1 characterized in that it is a member of the following group:

(+/−) 3,4-diethyl-2,3,3a,4,5,6-hexahydro-6-hydroxy-1H-indolo (3,2,1)(1,5) naphthyridine (+/−) 3,4,4-triethyl-2,3,3a,4,5,6-hexahydro 6-oxo-1H-indolo (3,2,1-de) (1,5) naphthyridine (+/−) methyl 3,4-diethyl-2,3,3a,4-tetrahydro-1H-indolo (3,2,1-de)(1,5) naphthyridine-6-carboxylate (+/−) methyl 3-ethyl-4-spirocyclohexyl-2,3,3a,4-tetrahydro 1H indolo (3,2,1-de)(1,5) naphthyridine (+/−) 3-ethyl-4-spirocyclohexyl-2,3,3a,4,5,6-hexahydro-6-oxo-1H-indolo (3,2,1-de)(1,5) naphthyridine.

8. Compounds according to claim 2 characterized in that R1 represents an ethyl group and R2 is a hydrogen atom.

9. Compound according to claim 6 characterized in that the hydrogens 3a and 4 are in a relative position having the cis configuration.

10. A pharmaceutical composition for the treatment of disorders resulting from insufficient cerebral oxygenation, characterized in that they comprise at least one of the compounds as defined in claim 1, in the form of a base or a pharmaceutically acceptable organic or inorganic acid addition salt thereof and a pharmaceutically acceptable carrier therefor.

11. A pharmaceutical composition for the treatment of disorders resulting from insufficient cerebral oxygenation, characterized in that they comprised at least one of the compounds as defined in claims 6 or 7, in the form of a base or a pharmaceutically acceptable organic or inorganic acid addition salt thereof and a pharmaceutically acceptable carrier therefor.

12. A pharmaceutical composition in the form of tablets, pills, syrups or injectable solutes in doses of from 0.5 to 700 mg of a compound according to claim 1.

13. A pharmaceutical composition in the form of tablets, pills, syrups or injectable solutes in doses of from 0.5 to 700 mg of a compound according to claim 6.

* * * * *